(12) United States Patent
Verbruggen et al.

(10) Patent No.: US 7,868,118 B2
(45) Date of Patent: Jan. 11, 2011

(54) HIGH REFRACTIVE INDEX FLEXIBLE SILICONE

(75) Inventors: Miriam Adrienne Lambertina Verbruggen, Zwolle (NL); Eelco Christoffer Brian van der Flier, Enschede (NL); Theodorus Adrianus Cornelius Flipsen, Groningen (NL); Hendrik Smit, Harkstede (NL)

(73) Assignee: Ophtec B.V., Groningen (NL)

( * ) Notice: Subject to any disclaimer, the term of this patent is extended or adjusted under 35 U.S.C. 154(b) by 634 days.

(21) Appl. No.: 11/740,563

(22) Filed: Apr. 26, 2007

(65) Prior Publication Data

US 2007/0203317 A1  Aug. 30, 2007

Related U.S. Application Data

(62) Division of application No. 10/360,113, filed on Feb. 7, 2003, now Pat. No. 7,217,778.

(60) Provisional application No. 60/355,070, filed on Feb. 8, 2002.

(51) Int. Cl.
*C08G 77/04* (2006.01)
(52) U.S. Cl. .......................................... 528/34; 528/43
(58) Field of Classification Search ................... 528/34, 528/43
See application file for complete search history.

(56) References Cited

U.S. PATENT DOCUMENTS 5,233,007 A * 8/1993 Yang ............................ 528/32

* cited by examiner

*Primary Examiner*—Kuo-Liang Peng
(74) *Attorney, Agent, or Firm*—Lucas & Mercanti, LLP

(57) ABSTRACT

The present invention discloses to a high refractive index polysiloxane (co)polymer comprising refractive index modifying groups chemically bonded in clustered configuration to the polysiloxane backbone. The invention also discloses methods for the preparation of such high refractive index polysiloxane (co)polymers A polysiloxane according to the invention is very suitable for use as a material for the production of intra-ocular lenses.

12 Claims, 3 Drawing Sheets

HIGH REFRACTIVE INDEX FLEXIBLE SILICONE

CROSS-REFERENCE TO RELATED APPLICATIONS

This application is a divisional of U.S. application Ser. No. 10/360,113 filed Feb. 7, 2003, now U.S. Pat. No. 7,217,778 which claims the benefit of priority from U.S. Provisional Application No. 60/355,070 filed Feb. 8, 2002, the contents of each are incorporated herein by reference.

FIELD OF THE INVENTION

The invention relates to a silicone material with a high refractive index. More particularly, it relates to a flexible silicone material with a high refractive index for use as an intra-ocular lens material, to intra-ocular lenses prepared from high refractive index polysiloxanes and to methods for their preparation.

BACKGROUND OF THE INVENTION

Prosthetic implant lenses are widely used to replace natural lenses that are affected by cataracts. Cataracts are the leading cause of blindness in the industrialized and developing world. The standard medical procedure for treatment is to remove the natural cloudy lens by elective cataract surgery and replace it with an intra-ocular lens.

Currently, flexible silicone is progressively replacing the classical polymethyl-methacrylate (PMMA) material and its derivative polymers as an intra-ocular lens implant material. Continued perfection of the cataract operation has brought new techniques that remove the natural lens through a self-sealing incision so tiny that no sutures are required. Thin, flexibly foldable implant materials permit the insertion of the implant lens through the same small size self-sealing incision of the cataract operation, which has the important advantage to considerably reduce the risk of post-operative complications.

Except for a preferred requirement of high flexibility, materials for intra-ocular lenses should be clear, highly transparent and should allow for the manufacturing of lenses with high refractive indices. An intra-ocular lens with a high refractive index has the advantage that it can be thinner at the same dioptric power as an intra-ocular lens with lower refractive index.

In order to increase the refractive index of intra-ocular lenses, co-polymers of polysiloxane and polymethacrylates may be prepared. Also, sulphur compounds can be introduced into the siloxane polymer. But despite these modifications, the refractive index of silicone materials is still limited, and a thin lens thereof does not provide much optical power.

It is recognized that the inclusion of diphenyl siloxane or phenyl-methyl siloxane into a polysiloxane results in a polymer of higher refractive index as disclosed in U.S. Pat. No. 3,996,189. Introduction of aromatic groups is now a general approach to increase the refractive index of intra-ocular lens materials while maintaining biocompatibility. Although other refractive index modifying groups such as cyclo-alkyl groups or aromatic groups, optionally combined with phenyl groups (JP2000017176) or phenol groups (U.S. Pat. No. 5,541,278), can also be used, conventional co-polymers for intra-ocular lenses consist of dimethylsiloxane-phenylmethylsiloxane co-polymers or dimethylsiloxane-diphenylsiloxane co-polymers as described in e.g. U.S. Pat. No. 5,147,396, JP10305092, EP 0335312, WO 93/21245, WO 95/17460, U.S. Pat. No. 5,444,106 and U.S. Pat. No. 5,236,970.

Thus, it is generally known that silicone materials with higher refractive index can be obtained by increasing the phenyl content of silicone (co)polymers. At a phenyl content of approximately 15 mole %, a polydimethyl siloxane/methylphenyl siloxane co-polymer has a refractive index of 1.462, (Gu & Zhou, *Eur. Polymer J.* 34, pp. 1727-33 [1998]). Although certain levels of refractive indices can be attained by using polymers and methods for their production as known in the prior art, there still is a need for materials with which intra-ocular lenses of a wide range of refractive indices, i.e. both high and low, can be produced.

Despite the positive effect on the refractive index, the introduction of refractive index modifying groups, such as phenyl-groups, in polysiloxanes is known to result in several important disadvantages.

A principal disadvantage is associated with the reduced flexibility or elongation of cross-linked networks of such modified polymers. The presence of phenyl groups attached to the alternating silicon-oxygen backbone of the siloxane causes the (co)polymer to become relatively stiff and, despite their potential dioptric power, the suitability of such polymers as a material for intra-ocular lenses is greatly reduced. In general, the introduction of aromatic groups, such as phenyl groups, in polysiloxane increases the glass transition temperature, or Tg, of the polymer, making it more hard and brittle and less flexible over a wider temperature range. This renders the material more vulnerable to cracking or breaking during folding and reduces the suitability of phenylated polysiloxanes as a material for intra-ocular lenses because such lenses must be folded and inserted through a self-sealing incision.

A well-known remedy to the problem of vulnerability to cracking is to reinforce the lens and improve its mechanical properties by combining the polymer with a solid filler material. Mostly, finely powdered silica is used as a filler material for this purpose. This filler material has a refractive index of 1.46. Since differences in the refractive index of the filler material and the polymer are not allowable in an optical lens, the maximum refractive index of a lens containing such filler material is ultimately 1.46.

Therefore, the use of silicone as an intra-ocular lens implant material and particularly the development of silicone with the enhanced material characteristics that would support broadening of such use is determined, at large, by the maximum attainable refractive index of the material and its associated flexibility. In order to obtain higher flexibility, the glass transition temperature of the material must be reduced. One method of reducing the glass transition temperature of phenyl-modified polysiloxanes is to link the phenyl-groups to the silicon-oxygen backbone by alkanediyl-bridges. Such modification of polysiloxanes is known from U.S. Pat. No. 4,780,510 wherein a hydride/vinyl reaction pair is used. U.S. Pat. No. 5,233,007, WO 93/21258 and U.S. Pat. No. 5,420,213 describe a process wherein phenyl groups are introduced in tetramethyl cyclo tetrasiloxane via an addition reaction with styrene to produce a tetramethylstyryl cyclo tetrasiloxane monomer.

However, another disadvantage associated with the introduction of refractive index modifying groups in polysiloxanes is related to the molecular weight of the polymer and the attainable mechanical strength of the polymer network in the silicone material. Polysiloxanes with a high content of phenyl groups generally exhibit a reduced molecular weight and therefore flexibility after crosslinking. This lower molecular weight reduces the mechanical strength of the network after cross-linking of the (co)polymers. In general, styrene-modified polysiloxanes or polysiloxanes with high phenylsiloxane content exhibit lower molecular weights compared to unmodified polysiloxane materials (i.e. with a low refractive index). This results in difficulties with achieving the high levels of flexibility, elasticity and mechanical strength of cross-linked rubbers. It is known, for example, that diphenyl cyclosiloxanes cannot easily be polymerized to high molecular weight polymers as a result of the unfavorable thermodynamics of the reaction from rings to chains (Journal of Polymer Science Part A: Polymer Chemistry, v35(10), p 1973). Only the application of non-equilibrium reaction conditions will yield the desired product, but such conditions are perceived as less suitable for large-scale production.

Thus, the introduction of refractive-index modifying groups in polysiloxanes results in reduced flexibility of the silicone prepared therefrom and in reduced mechanical strength due to the presence of relatively low molecular weight polysiloxanes and reduced flexibility of the polymer chains themselves.

Yet another important factor to consider in preparing polysiloxanes for intra-ocular lens applications relates to the presence of free reactive groups in the final material. The methods as described in U.S. Pat. No. 4,780,510 yield products wherein the presence of free unreacted vinyl groups in the polymer after completion of the addition and cross-linking reaction cannot be avoided nor controlled. This is not useful in intra-ocular lens applications, as it may result in allergy, inflammation or other discomforts in patients.

SUMMARY OF THE INVENTION

Surprisingly it was found that the refractive index of siloxane polymers is increased considerably without compromising the mechanical properties of the material, when refractive index modifying groups are bonded to the siloxane backbone via an alkanediyl-bridge in a clustered configuration. Despite the presence of high numbers of refractive index modifying groups a high refractive index polysiloxane (co)polymer is obtained of which the mechanical properties are minimally affected. The advantageous material characteristics of silicone prepared therewith are essentially maintained.

Although the mechanical properties of the individual (co)polymers are slightly affected, this effect is small, so that a silicone material prepared by cross-linking of the individual polymers exhibits such beneficial properties that the polysiloxanes of the invention may suitably be used for the manufacture of intra-ocular lenses.

Basically the polysiloxanes may be prepared by one of two routes; i) via an addition reaction between clustered configurations of refractive index modifying groups and cyclic siloxane monomers followed by one of several methods of polymerization to obtain a (co)polymer, also termed the monomer-route hereinbelow, or (ii) via an addition reaction between clustered configurations of refractive index modifying groups and a (co)polymer (pre-polymer), also termed the polymer-route hereinbelow.

The present invention therefore provides a high refractive index (cyclic) siloxane monomer comprising a clustered configuration of refractive index modifying groups chemically bonded to the siloxane backbone via an alkanediyl-bridge such that one alkanediyl-bridge binds at least two refractive index modifying groups to said backbone.

The present invention also provides a high refractive index siloxane (co)polymer, comprising a clustered configuration of refractive index modifying groups chemically bonded to the polysiloxane backbone via an alkanediyl-bridge such that one alkanediyl-bridge binds at least two refractive index modifying groups to said backbone.

By introducing more than one refractive index modifying group at each alkanediyl-bridge, relatively high refractive indices can be attained whilst only a limited number of modifications is required. When, for example, a cluster of three phenyl groups is bonded to a siloxane backbone via an alkanediyl-bridge, the contribution to the refractive index per modification will be about three times as high as when a styrene is bonded to a siloxane backbone.

The attainable refractive indices of the new high refractive index polysiloxane (co)polymer material may reach such high values, that copolymerizing with conventional and even unmodified polysiloxanes is possible or even necessary for use in an intraocular lens while maintaining a relatively high refractive index in the resulting (co)polymer. Additionally high refractive index polysiloxane (co)polymer material may directly be obtained.

The (co)polymers of the invention exhibit high molecular weights so that after cross-linking the resulting material is strong and flexible. The material attains these mechanical properties, whilst having a high refractive index, due to the fact that the refractive index modifying groups are bonded to the backbone of the siloxane in a clustered configuration via alkanediyl-bridges, such that one alkanediyl-bridge binds at least two refractive index modifying groups to said backbone.

The polymers of the invention are essentially not crosslinked so that processing and handling thereof in the manufacture of intra-ocular lenses is possible.

The number of unreacted crosslinkable groups that remain in the polymer upon its preparation is so small that these groups substantially completely disappear during and after cross-linking of the polymer. This is necessary to obtain a biocompatible material.

Therefore, based on the high refractive index polysiloxanes of the present invention, high refractive index silicone materials of good mechanical strength and with a large possible range of values for the refractive index can be obtained, i.e. both very high and reduced. Such silicone materials constitute an excellent material for, e.g., intra-ocular lenses.

The present invention provides for intra-ocular lenses comprising a high refractive index polysiloxane (co)polymer, said high refractive index polysiloxane (co)polymer comprising a clustered configuration of refractive index modifying groups chemically bonded to the polysiloxane backbone via an alkanediyl-bridge such that one alkanediyl-bridge binds at least two refractive index modifying groups to said backbone. Such an intra-ocular lens may attain high refractive index values whilst being flexible enough to be folded.

The present invention also provides methods for the preparation of high refractive index siloxane monomers and siloxane (co)polymers according to the invention, methods for preparing high refractive index siloxane (co)polymers therewith. Said methods for the preparation of high refractive index siloxane (co)polymers are relatively easy to control and do not lead to large batch-to-batch quality variations. These methods and the materials resulting thereof are required for the mass manufacturing of intra-ocular lenses. Therefore, the present invention also provides methods for the preparation of intra-ocular lenses.

DETAILED DESCRIPTION OF THE INVENTION

As used herein, the term alkyl group refers to a straight chain or a branched-chain alkyl radical containing from 1 to 20, preferably from 1 to 10, more preferable from 1 to 3, carbon atoms. The alkyl radical may be optionally substituted with one or more substitutents that comprise of elements such as oxygen, nitrogen, sulphur, halogen (Cl, Br, I, F), hydrogen and phosphorus and may comprise alkoxy, hydroxy, amino, nitro or cyano.

The term (cyclo)alkyl group refers to an alkyl radical or a cyclic alkyl radical. The latter includes saturated or partially saturated monocyclic, bicyclic or tricyclic alkyl radicals wherein each cyclic moiety contains 3 to 8, preferably 4 to 8, carbon atoms. Examples of such radicals include methyl, ethyl, n-propyl, isopropyl, n-butyl, isobutyl, sec-butyl, tert-butyl, pentyl, isoamyl, hexyl, octyl, cyclopentyl, cyclopentenyl, cyclohexenyl, and cyclohexyl and are understood to include (cyclo)alkyl groups optionally substituted with substitutents that comprise of elements such as oxygen, nitrogen, sulphur, halogen, hydrogen and phosphorous and may comprise alkyl, alkoxy, hydroxy, amino, nitro or cyano.

The term aromatic group refers to the monocyclic and polycyclic aromatic hydrocarbons, or arenes, and their substitution products such as benzene, naphthalene, toluene as well as to the hetero-aromatic, or aromatic heterocyclic structures, such as thiophene and pyridine.

The term aryl group refers to radicals comprising an aromatic or hetero-aromatic ring system derived from arenes by removal of a hydrogen atom from a ring carbon atom, such as a phenyl, naphtyl or anthracene radical which may optionally carry one or more substitutents that comprise of elements such as oxygen, nitrogen, sulphur, halogen (Cl, Br, I, F), hydrogen and phosphorous and may comprise alkyl, alkoxy, hydroxy, amino, nitro or cyano. Examples of such radicals include phenyl, p-tolyl, 4-methoxyphenyl, 4-(tert-butoxy) phenyl, 4-chlorophenyl, 4-hydroxyphenyl, 1-naphtyl, and 2-naphtyl. It is to be noted that fused and connected rings, as well as 5, 6, 7 or 8 membered rings, such as cyclopentadienyl, imidazolyl, thiophenyl, thienyl, etc. are included. In the context of the present invention, aryl groups will be understood to include the arene-derived bivalent arylene groups, such as o-phenylene and the arynes, such as benzyne.

The term arylalkyl group means an alkyl radical as defined above in which one hydrogen atom is replaced by an aryl radical as defined above, such as benzyl, or 2-phenylethyl.

Allyl refers to propene radicals $(CH_2)_2CH$.

Figure 2:
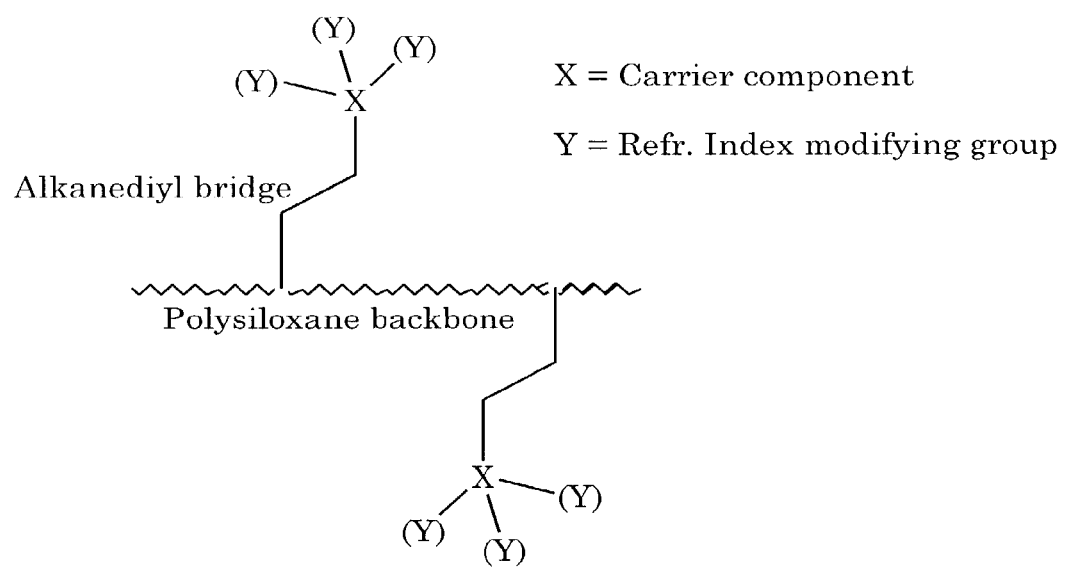
FIG. 2 represents the clustered configuration wherein the refractive index modifying groups are positioned in the high refractive index siloxane (co)polymers of the present invention and identifies the polysiloxane backbone, the alkanediyl-bridge, the carrier component (X) and the refractive index modifying groups (Y).

A high refractive index siloxane (co)polymer according to the invention may be prepared by chemically modifying a monomeric cyclic siloxane precursor through a vinyl/hydride addition reaction with a carrier component (X in FIG. 2) containing at least two refractive index modifying groups (Y in FIG. 2) in the presence of an addition reaction catalyst and (co)polymerizing the modified monomeric siloxane precursor. Use may be made of monomeric cyclic siloxane precursors that contain reactive groups such as hydride groups or vinyl groups as a precursor material for a high refractive index siloxane (co)polymer. Such precursors are commercially available (e.g. Petrarch® product line, United Chemical Technologies, Inc., Bristol, Pa., USA) and support well controlled addition reactions according to the invention.

Figure 1:
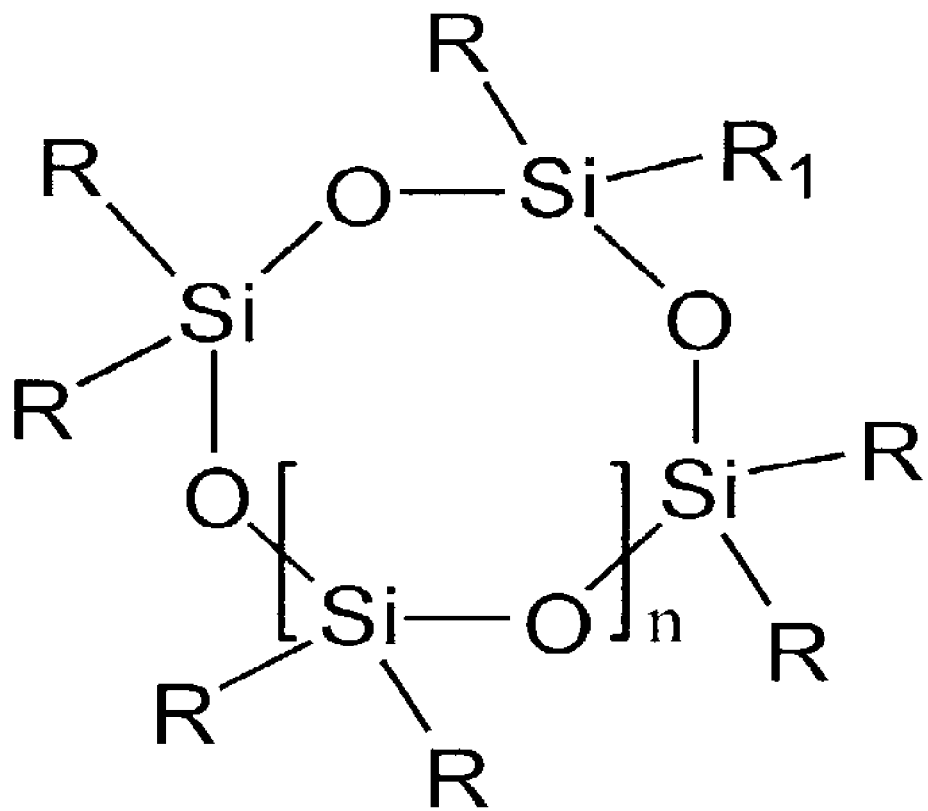
FIG. 1 represents a cyclic siloxane that may be used as a monomeric precursor for the preparation of a high refractive index siloxane (co)polymer according to the invention.

A monomeric cyclic siloxane precursor that is used in embodiments of the present invention may include three or more, preferably 3 to 6, more preferably 3 or 4 silicon atoms alternated with oxygen atoms in a cyclic structure such as presented in FIG. 1. In this figure, n is preferably 0, 1, 2 or 3, more preferably 0 or 1; R is independently alkyl, vinyl or hydride; $R_1$ is hydride or, in an alternative embodiment, vinyl. A monomeric cyclic siloxane precursor according to the invention may comprise from 1 to 12, preferable from 2 to 6, more preferable from 2 to 4 reactive groups in the form of vinyl or hydride groups.

A carrier component (X) can advantageously be bonded to a silicon atom of the precursor through a vinyl/hydride addition reaction, such as a hydrosilylation reaction. To support such a reaction, the precursor may contain one or more hydride groups bonded to silicon atoms of the cyclic siloxane, in which case the carrier component would comprise a reactive vinyl group.

In an alternative embodiment, it is possible to use a precursor monomer, comprising one or more reactive vinyl groups bonded to the silicon atoms of the cyclic siloxane to which the carrier component with the refractive index modifying groups (Y) can effectively be bonded. In such a case, the carrier component would preferably comprise a vinyl reactive hydride group.

The position and distribution of the reactive groups in a precursor monomer is not critical.

One or more carrier components (X) containing at least two refractive index modifying groups (Y) can be bonded to each precursor monomer. In one embodiment a cyclic siloxane precursor is modified via an alkanediyl-bridge with only one carrier component (X) containing at least two refractive index modifying groups (Y) attached thereto.

In alternative embodiments several or all of the silicon atoms in a cyclic siloxane precursor molecule may have bonded two carrier components (X), each carrying at least two refractive index modifying groups (Y), via alkanediyl-bridges. This latter situation will result in high numbers of refractive index modifying groups in the eventual polysiloxane and a high refractive index of the silicone. The number of carrier components bonded to the precursor monomers may be selected such that a desired refractive index in the eventual polysiloxane material is obtained.

The present invention therefore also provides a monomeric cyclosiloxane comprising a clustered configuration of refractive index modifying groups chemically bonded to the siloxane backbone via an alkanediyl-bridge such that one alkanediyl-bridge binds at least two refractive index modifying groups to said backbone. Such a monomeric cyclosiloxane is very useful in preparing a (co)polymer of the present invention.

Based on the above, a large number of useful precursor materials for the preparation of high refractive index siloxane (co)polymers according to the present invention can be identified by those skilled in the art. Among these are cyclic hydride-containing siloxane monomeric precursors. Also cyclic vinyl-containing siloxane precursors, such as pentavinyl pentamethyl cyclo pentasiloxane, can be used in embodiments of the present invention. Particularly useful precursors are tetrahydro tetramethyl cyclosiloxane and tetravinyl tetramethyl cyclo tetrasiloxane.

Figure 3:
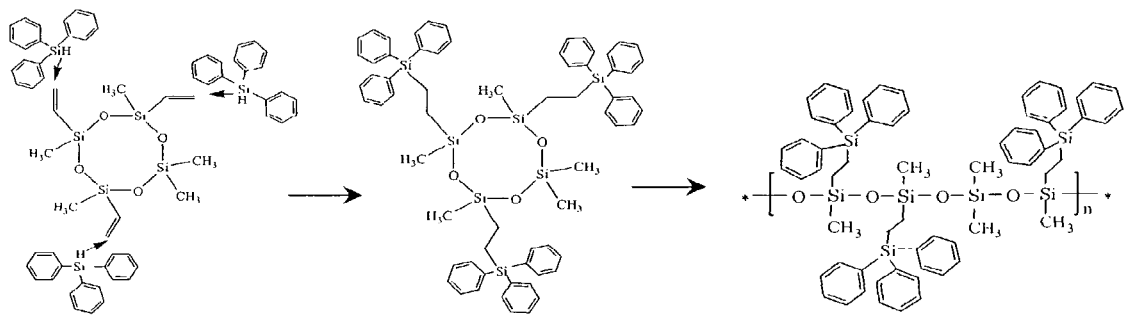
FIG. 3A represents an embodiment of the present invention wherein an addition reaction between triphenylsilane and trivinyl pentamethyl cyclo tetrasiloxane and the resulting high refractive index siloxane (co)polymer is illustrated.
FIG. 3B represents an embodiment of the present invention wherein an addition reaction between triphenylsilane and a divinyl hexamethyl tetrasiloxane polymer and the resulting high refractive index siloxane (co)polymer is illustrated.
Figure 3:
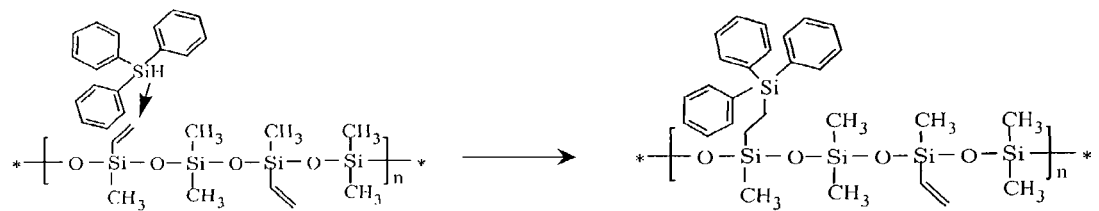

As stated, in a favorable embodiment a carrier component containing at least two refractive index modifying groups is reacted with a monomeric cyclic siloxane precursor as described (FIG. 3A).

Preferably, the bonding of the carrier component (X) containing at least two refractive index modifying groups (Y) results in a situation wherein it is separated or spaced apart from the silicon atom to which it is most directly bonded. Such spacing can very advantageously be accomplished by using an alkanediyl-bridge between the carrier component and the silicon atom. A very useful reaction pair is therefore formed by an hydride/vinyl reaction pair, whereby one member of said reaction pair is present on the monomeric cyclic siloxane precursor and the other member of said reaction pair is present on the carrier component that contains the refractive index modifying groups, because such a reaction results in an alkanediyl-bridge, in particular an ethanediyl-bridge.

An alternative reaction pair may comprise a hydride/allyl reaction pair, which also results in an alkanediyl-bridge, in particular a propanediyl-bridge.

In the light of the above, other suitable reaction pairs will be obvious to the person skilled in the art.

To obtain a high refractive index siloxane (co)polymer according to the invention, a large number of refractive index modifying groups (Y) can be used. Both cyclic, straight chain and branched chain hydrocarbons are suitable. Preferably, aromatic groups, aryl groups, arylalkyl groups, cycloalkyl groups and/or branched alkyl groups are used as refractive index modifying groups (Y) in embodiments of the present invention. More preferably, phenyl groups are used as refractive index modifying groups.

One carrier component (X) may carry two or more, preferably three, refractive index modifying groups (Y). The carrier component (X) may comprise a single or multi-atom structure. The carrier component (X) may suitably comprise a silicon atom to which the refractive index modifying groups (Y) are bonded, in which case the silicon atom serves as the central atom of a clustered configuration of refractive index modifying groups. However, other atoms may also be comprised by the carrier component (X). Instead of silicon, phosphorus, nitrogen, germanium or carbon may for example be used as the central atom of a clustered configuration of refractive index modifying groups. The choice for the carrier component (X) is not critical as long as at least two refractive index modifying groups (Y) can be bonded thereto and as long as it can be attached to a silicon atom of a cyclic siloxane via an alkanediyl-bridge.

Preferably, the carrier component is bonded to a cyclic siloxane monomer with the refractive index modifying groups already attached to the carrier component. A clustered configuration of refractive index modifying groups according to the invention therefore preferably comprises a carrier component (X) with the refractive index modifying groups (Y) already attached. A clustered configuration of refractive index modifying groups (X+Y) according to the invention can suitably be introduced into a cyclic siloxane monomer by using compounds such as triphenylsilane, diphenylsilane, triphenyl dimethyl disiloxane, diphenyl alkyl dimethyl disiloxane, all of which will readily react with a vinyl-containing siloxane precursor and wherein carrier and refractive index modifying groups are combined.

Also very suitable compounds for introducing a clustered configuration of refractive index modifying groups into a cyclic siloxane monomer are compounds such as triphenyl vinylsilane, diphenylalkyl vinylsilane, phenyldialkyl vinylsilane, triphenyl dimethylvinyl disiloxane, diphenylethene, 3,3,3-triphenyl-1-propene, 3,3-diphenyl-1-propene or any other vinyl reactive polyphenyls, all of which will readily react with a hydride-containing siloxane precursor.

Triphenylsilane and triphenyl vinylsilane are preferred compounds by which a clustered configuration of refractive index modifying groups can be introduced in polysiloxane precursors and/or polysiloxanes of the present invention. The person skilled in the art will readily understand from the above which alternative compounds may be used for introducing a clustered configuration of refractive index modifying groups into a cyclic siloxane monomer.

In one embodiment, a method for preparing a high refractive index siloxane (co)polymer of the invention comprises the steps of a) chemically modifying a cyclic siloxane by performing an addition reaction in the presence of an addition reaction catalyst which reaction links to the siloxane backbone of said cyclic siloxane a clustered configuration of refractive index modifying groups via an alkanediyl-bridge such that at least two of said refractive index modifying groups are bound to said backbone via a single alkanediyl-bridge and b) facilitating subsequent polymerization of the resulting reaction products thereby obtaining the high refractive index siloxane (co)polymer.

In certain aspects of the invention, the cyclic siloxane is one corresponding to Formula II which is also depicted in FIG. 1:

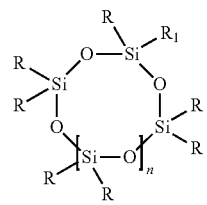

wherein
R is independently alkyl, vinyl or hydride;
$R_1$ is vinyl; and
n=0, 1, 2 or 3.

The above described method for preparing a high refractive index siloxane (co)polymer harbours many advantages over methods of the prior art and can favorably be used for the preparation of high refractive index siloxane (co)polymers suitable for the production of intra-ocular lenses.

In an alternative embodiment it is possible to perform addition reactions to polysiloxanes (see FIG. 3B). In order to perform such addition reactions to polymers, solvents such as methanol or toluene may facilitate lowering the viscosity of the preparation. Due to the solvent-associated dilution of reactive groups present in the reaction mixture, and the resulting reduced reaction rate, reaction temperatures may be elevated and/or longer reaction periods may be used.

Although addition reactions to polysiloxanes are very suitable in methods of the present invention, they generally require more proper control of reaction conditions than addition reactions to cyclic monomers as described above. Additionally, the reaction efficiency, i.e. the degree to which the addition reaction has occurred is generally less than in addition reactions to cyclic monomers. A polymeric material of the invention with a high value for the refractive index may also be prepared by using the addition reaction to the monomeric cyclo siloxanes as described above. On the other hand, the molecular weight of the individual molecules of polysiloxane polymers of the invention is generally better controllable when clustered configurations of refractive index modifying groups are added to siloxane (co)polymers with predetermined molecular weight. The higher molecular weight, obtainable by this embodiment, favors the strength of the resulting crosslinked high refractive index polymer. Generally, the fraction of the polymeric material modified, the molecular weight of the polymer and the amount and the distribution of reacted groups in the eventual polymer and therefore the refractive index as well as the mechanical properties of the eventual material may be properly controlled by the person skilled in the art based on the description provided herein.

In order to prepare a polysiloxane of the invention, suitable for use in an intra-ocular lens, the person skilled in the art is able to select a suitable siloxane (co)polymer in combination with a carrier group. Depending on the addition reaction employed, reactive groups on the polysiloxane may be suitably selected. A very suitable (co)polymer is for example a combination of dimethylsiloxane and vinylmethylsiloxane. The starting (co)polymer should be of high molecular weight so that cross-linking of the modified (co)polymer results in a strong, yet flexible network. Preferably, the solvent is dried and purified by distillation prior to use. The reactive groups, such as vinyl groups, are preferably arranged randomly, i.e. distributed uniformly, across the polymer to minimize effects such as steric hindrance during modification and inhomogeneously cross-linking. This may for example be achieved by allowing sufficient time for copolymerization to occur between cyclosiloxanes (e.g. octamethyl cyclo tetrasiloxane and tetravinyl tetramethyl cyclo tetrasiloxaan).

The percentage or amount of reactive groups, such as vinyl groups, in the copolymer used in the polymer route for preparing a high refractive index polysiloxane of the invention is preferably optimized. The amount of reactive groups is preferably adequately high to allow sufficient refractive index modifying groups (e.g. triphenylsilane groups) to be bonded during the modification (addition) reaction (sufficient herein referring to the desired refractive index). However, the amount of reactive groups is preferably low enough to result in an almost complete modification reaction, i.e. such as to result in a low amount of unreacted groups left in the polymer that allow appropriate cross-linking of the polymer molecules in a cross-linking reaction. The duration of a reaction at a certain reaction-temperature may be optimized to allow for remaining reactive groups in the co-polymer suitable for performing a cross-linking reaction therebetween.

When a clustered configuration of refractive index modifying groups, such as triphenylsilane, is reacted with a cyclic siloxane precursor, such as tetravinyl tetramethyl cyclo tetrasiloxane according to one method of the invention, the reactive groups of the precursor can be subjected to an addition reaction in a very controlled manner. By selecting suitable values for reaction parameters such as time, temperature and addition reaction catalyst concentration, the reactive groups of the precursor can be modified to any desired level, even essentially completely.

An advantage of the addition reaction to cyclic monomers of the present invention is that the product resulting from the addition reaction (wherein the cyclic monomers are modified through the addition of carrier compounds with refractive index modifying groups) can be purified more easily than viscous polysiloxanes produced by methods of the prior art. When preparing a polysiloxane of the present invention under optimal conditions for the addition reaction to a cyclic monomer, a very small number of unreacted reactive groups usually remain. Under these circumstances, co-polymerization may for example require the incorporation of extra vinylsiloxane units to reach the amount of free vinyl groups advantageous for proper cross-linking at high molecular weights of the polymer (usually about 1-5 mole %).

Conversely, polysiloxanes with refractive index modifying groups prepared by methods of the prior art usually possess free unreacted reactive groups in uneven distribution or to an uncontrolled extent, which hampers effective control of both the cross-linking reaction and the addition reaction. Therefore, the inventors have found that in order for it to be suitable for use in an intra-ocular lens, a polysiloxane comprising a clustered configuration of refractive index modifying groups chemically bonded to the polysiloxane backbone via an alkanediyl-bridge may be prepared by first completing the addition reaction between the clustered configurations of refractive index modifying groups and the polysiloxane polymer, and then cross-linking the resulting polymer to obtain a high refractive index silicone material, whereby the amount of unreacted reactive groups is substantially reduced over methods of the prior art and whereby no undesired side-reactions occur such as premature gelling as a result of the presence of high levels of unreacted reactive groups. An important advantage of this method is further that the resulting high refractive index polysiloxane polymer is suitable for use in injection molding for the preparation of intra-ocular lenses.

In one embodiment of a method of the invention, wherein addition reactions to the monomeric precursor are performed, results in an uniform distribution of reactive index modifying groups. Further, the reaction may take place at relatively low temperatures and relatively shorter reaction times compared to addition to a polymer, whereby the incidence of undesired cross-linking between reactive groups of the individual precursors is reduced.

(Co)polymerization catalyst are used when a process for the preparation of a polysiloxane according to the invention is performed with certain combinations of cyclic siloxane monomers and siloxane monomer modified with clustered configurations of refractive index modifying groups.

Without wishing to be bound by the exact mechanism of the reaction, the high refractive index siloxane (co)polymer or alternatively the siloxane oligomers or monomers are an aspect of the present invention. In fact, the terms "modified monomer", "siloxane (co)polymer" or "polymer" with reference to the product resulting from the modification reaction of monomeric cyclic siloxanes as herein described, is herein defined as the reaction product of an addition reaction wherein cyclic siloxane monomers are modified with clustered configurations of refractive index modifying groups in any state.

In a favorable embodiment, a reaction mixture for performing an addition reaction according to the present invention preferably comprises a cyclic siloxane and clustered configurations of refractive index modifying groups in a molar ratio of about 10:1 to about 1:10, more preferably of about 1:1 to about 1:10, even more preferably of about 1:4. Such a reaction mixture further preferably comprises an addition reaction catalyst in an amount depending on the type of catalyst, but in the case of platinum divinyl tetramethyl disiloxane an amount of about 1-200 ppm, preferably of about 10 ppm can be used. Optionally, a reaction mixture may comprise additives such as vinyl or hydride reactive UV-blockers. It is advantageous to exclude air from the reaction mixture. The reaction preferably takes place under an inert atmosphere, such as a nitrogen atmosphere.

Suitable reaction conditions include a reaction temperature of about 30-150° C., preferably about 70-100° C. and most preferably about 90° C. The mixture is preferably stirred at the reaction temperature and the reaction is allowed to take place for a period of about 6-168 hours, preferably 72-120 hours. Optionally, the reaction can be stopped at 50-99% of the maximum level of additions.

A particularly suitable method for the preparation of a high refractive index siloxane (co)polymer of the invention comprises the modification of the cyclic siloxane precursor tetravinyl tetramethyl cyclo tetrasiloxane with triphenylsilane, which is exemplified in example 1. A schematic representation of the modification of trivinyl pentamethyl tetrasiloxane with triphenylsilane is illustrated in FIG. 3A.

As an addition reaction catalyst, any catalyst for hydrosilylation such as platinum group metal components or Speiers catalyst can be used. In a preferred embodiment Karstedt catalyst (platinum divinyl tetramethyl disiloxane) is used.

An alternative reaction route for the preparation of a high refractive index siloxane (co)polymer of the invention is formed by producing the clustered configuration of refractive index modifying groups as a Grignard-reagent and contacting this reagent with a cyclic hydride-containing siloxane precursor. Such a method is well known in the art.

A high refractive index siloxane (co)polymer may be prepared according to a preferred method of the invention by performing the addition reaction to a cyclic siloxane monomer and copolymerizing this monomer with other cyclic siloxane monomers (termed co-monomers hereinafter) or with other (low refractive index) polysiloxanes to obtain (co) polymers of a specific refractive index or with increased flexibility, increased mechanical strength or with a variety of functional groups (e.g. cross-linking enhancing groups such as vinyl or hydride groups in Pt-catalyzed systems or alkoxy groups).

An important characteristic of the (co)polymers in view is that their degree of polymerization is sufficiently high. The crosslink density can then be low and an elastic material with sufficient strength for the use in foldable intraocular lenses is obtained. After cross-linking, transparent materials with a tensile strength of 1 MPa (minimum) and an elongation at break of 50% (minimum) should be obtained. Another important characteristic is the fact that the refractive index modifying groups are introduced into the (co)polymer before crosslinking takes place for both the monomer and polymer routes of synthesis. The high refractive index (co)polymers can be purified before further use. The uncrosslinked polymers of this invention can be used for injection molding. In a typical two-component system a crosslinker is added to one part and a catalyst to the other. Curing takes place in the mold.

Thus, high refractive index siloxane (co)polymers can be derived from high refractive index siloxane (co)polymers or monomers according to the invention in one of several ways.

For example, a high refractive index siloxane (co)polymer or monomer can be mixed with other polysiloxanes, in the presence of a (co-)polymerization catalyst (and optionally a solvent), and allowed to co-polymerize thereby forming a high refractive index polysiloxane (co)polymer Also, a high refractive index polysiloxane can be prepared by preparing a (co)polymer or modified monomer according to the invention and reacting said (co)polymer or modified monomer with a cyclic siloxane co-monomer in the presence of a (co)polymerization catalyst.

A large number of cyclic co-monomers are suitable for use in the above-described co-polymerization for the preparation of a high refractive index siloxane (co)polymer according to the invention. Co-monomers may or may not comprise refractive index modifying groups themselves. They may or may not comprise reactive groups, such as hydride or vinyl groups. Examples of cyclic co-monomers that can be co-polymerized are cyclic co-monomers or co-monomers selected from the group consisting of tetravinyl tetramethyl cyclo tetrasiloxane, trivinyl trimethyl cyclo trisiloxane octamethyl cyclo tetrasiloxane, hexamethyl cyclo trisiloxane, trimethyl triphenyl cyclo trisiloxane, tetramethyl tetraphenyl cyclo tetrasiloxane, trifluoropropyl methyl cyclo trisiloxane, hexaphenyl cyclo trisiloxane and octaphenyl cyclo tetrasiloxane or (co)polymers derived from these cyclic (co)monomers.

One method for preparing a (co)polymer according to the invention may comprise the purification of a triphenyl modified siloxane monomer by stirring it in boiling methanol and recovering it by precipitation and decanting the boiling methanol. The resulting white paste can be dried in a vacuum oven until a transparent material is obtained. At room temperature such material may appear as a glassy solid. This material can then be mixed with octamethyl cyclo tetrasiloxane and a small amount of tetravinyl tetramethyl cyclo tetrasiloxane. Then, a (co-)polymerization catalyst such as potassium silanolate dissolved in purified, dried dimethyl sulfoxide (DMSO) can be added, preferably $10^{-6}$ to $10^{-5}$ mole of potassium silanolate per gram of mixture is used. The mixture is reacted at a reaction temperature of between 10-200° C., but preferably 150-200° C. under inert atmosphere (nitrogen). Reaction then may preferably take place under an inert atmosphere for a duration of between 1-400 hours, until a transparent viscous material is formed. Preferably the reaction time is 96 hours or more to obtain complete randomization of siloxane groups in the co-polymer. Instead of potassium silanolate, other basic catalysts may be used as (co-)polymerization catalyst, such as potassium hydroxide or sodium hydroxide. The presence of DMSO is not essential but increases the reaction rate for potassium salts. Tetravinyl tetramethyl cyclo tetrasiloxane can also be added after copolymerisation of octamethyl cyclo tetrasiloxane and the modified monomer and copolymerised in a the next step at about 100° C. to avoid the formation of gel due to a high concentration of reactive vinylgroups.

When preparing a polymer of the invention by an alternative route, i.e., by the polymer route as illustrated in FIG. 3B, a clustered configuration of refractive index modifying groups may be reacted with any polysiloxane homopolymer, more preferably with a siloxane (co)polymer, of high molecular weight. The molecular weight should preferably measure between 5,000 and 1,000,000 g/mole, more preferable between 10,000 and 500,000.

For example, an addition reaction of a triphenylsilane, as a clustered configuration of refractive index modifying group, may be performed to a siloxane (co)polymer comprising a limited number of vinyl groups. The number of vinyl groups in the (co)polymer should be chosen such that a modified (co)polymer is obtained that contains a relatively low amount of remaining unreacted vinyl groups, said low amount being essentially completely removable by a suitable cross-linking reaction between said modified (co)polymer and a suitable cross-linker for the preparation of a silicone material. The amount of remaining unreacted vinyl groups before crosslinking should preferably amount to a mole percentage between 1 and 10, most preferably between 2 and 5.

The high refractive index (co)polymers of the present, invention may be co-polymerized or re-arranged with other high refractive index (co)polymers of the present invention or still other polysiloxanes or cyclo siloxanes to prepare a (co) polymer with a desired refractive index.

(Co)polymers with a refractive index varying from 1.4 to about 1.6 can be produced by co-polymerization of highly phenylated siloxane polymers and siloxane polymers with a lower degree of aromatic substitution or even phenyl-free siloxane polymers using a method described hereinabove.

Co-polymers according to the invention have the formula:

Formula (I):

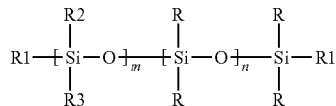

wherein R is independently selected from alkyl radicals, substituted alkyl radicals, aryl radicals, substituted aryl radicals, aromatic radicals such as naphtyl radicals, cycloalkyl radicals, arylalkyl radicals, allyl radicals, vinyl and hydride;

R1 is independently selected from alkyl radicals, substituted alkyl radicals, aryl radicals, substituted aryl radicals, aromatic radicals such as naphtyl radicals, cycloalkyl radicals, arylalkyl radicals, allyl radicals, vinyl and hydride, monovalent hydrocarbon radicals having a multiple bond or substituted equivalents thereof, monovalent hydrocarbon radicals having a siliconhydride group, and triphenylsiloxane groups, but preferably comprises a vinyl or hydride group;

R2 is preferably a triphenyl silylalkyl radical, but can be selected from the group of triarylsilyl alkyl radicals, diarylalkyl silylalkyl radicals, aryl dialkylsilyl alkyl radicals, trialkyl alkylsilyl radicals, tricycloalkyl silylalkyl radicals, dicycloalkyl alkylsilyl alkyl radicals, cycloalkyl dialkyl silylalkyl radicals;

R3 is independently selected from alkyl radicals, substituted alkyl radicals, aryl radicals, substituted aryl radicals, aromatic radicals such as naphtyl radicals, cycloalkyl radicals, arylalkyl radicals, allyl radicals, vinyl and hydride, but is preferably an alkyl radical, more preferably a methyl radical;

m is between 10 and about 2,000,000, preferably between about 100 and about 100,000;

n is between 10 and about 2,000,000, preferably between about 100 and about 500,000; most preferably, m and n are values that result in a molecular weight of the polymer that is high enough to result in a strong and flexible material after cross-linking of said polymer.

As end blocking groups for example divinyl tetramethyl disiloxane can be used.

The polymeric resin may further contain endgroups (empirical formula $R_3SiO_{0.5}$), and branching points and T-resins (empirical formula $RSiO_{1.5}$) and tetra-functional units (empirical formula $SiO_2$), structures known to those skilled in the art, to improve material properties for the application involved. These organopolysiloxane (co)polymers are known in the art as MQ resins.

The polymeric resin may also contain alkylgroups between polysiloxane chains as bridging groups obtainable by e.g. end-linking.

The presence of unreacted vinyl groups as part of siloxane (co)monomers or (co)polymers, allows cross-linking of the (co)polymer as described earlier. Unreacted vinyl groups may also deliberately be introduced by choosing reaction conditions in such a way that not all reactive groups (such as hydride or vinyl groups) on the precursor monomers have reacted. The presence of such unreacted vinyl groups is then deliberately introduced in a polysiloxane of the invention in order to enable performance of a cross-linking reaction. The performance of additional cross-linking then results in a polymer having good mechanical properties for use in an intra-ocular lens.

As cross-linkers, any siloxane (co)polymer with hydride groups or with vinyl groups can be used in a method of the present invention, depending on the composition of the polymer that is to be cross-linked. For example, co-polymers of methyl hydrosiloxane and phenyl methylsiloxane, co-polymers of methyl hydrosiloxane and diphenylsiloxane, and co-polymers of methyl vinylsiloxane and phenyl methylsiloxane and/or combinations of such compounds can be used. In addition, monomeric crosslinkers such as e.g. tetrakis (dimethylsiloxy)silane, dimethylsilane, methylsilane and/or 1,1, 3,3-tetramethyl disiloxane can be used as cross-linking reagent. Alternative cross-linking systems can also be used.

Functional groups that contribute to cross-linking can be introduced in the (co)polymer. Examples are alkoxy, acetoxy, ketoxime, amine, (meth)acrylate and epoxy functional siloxane (co)polymers. (Meth)acrylate containing units such as acryloxypropyl can undergo UV—and visible light cross-linking when suitable photo-initiators are present. Epoxy-modified siloxane units e.g. can undergo electron beam curing.

Cross-linking preferably should not proceed too rapidly at room temperature. In order to improve handling and control processing times, for example required during mixing of different (co)polymer components and injection molding, cross-linking inhibitors such as 1,2,3,4-tetramethyl-1,2,3,4-tetravinyl-cyclotetrasiloxane may be used. Such inhibitors may be added to the reaction mixture of the addition reaction in amounts of 0.01-10 wt. % based on the weight of the polymer.

Prior or during polymerization or co-polymerization or cross-linking, additives such as UV-blocking agents or other additives such as dyes may be administered to the reaction mixtures. As UV blocking agents, vinyl functional or hydride functional benzotriazol, vinyl functional or hydride functional 2-hydroxy benzophenones, allyl benzophenones (monoallyl benzophenone) and vinyl functional or hydride functional benzotriazoles may be used in amounts of 0.01-5 wt. % based on the weight of the polymer.

A high refractive index siloxane (co)polymer or modified monomeric precursor according to the present invention preferably exhibits a refractive index of at least 1.4, more preferably at least 1.65. In accordance with the invention the refractive index is measured by Abbé-type refractometry.

High refractive index siloxane (co)polymers according to the present invention are very suitable for use in a multitude of applications. Especially in those applications where light refraction or optical appearance is important, such as in optical lenses, optical fibers, intra-ocular devices such as intra-ocular lenses for cataract, refractive and reconstruction surgery as well as for occluders and tear duct devices, in contact lenses, ophthalmic applications, glasses, windows, windshields, transparent coatings and in cosmetic products like hair care products the material of the present invention can be beneficially applied. In a most preferred embodiment, the high refractive index siloxane (co)polymers of the present invention are used for the manufacture of intra-ocular lenses.

Formation of intra-ocular lenses or optics from the high refractive index siloxane (co)polymers of the present invention may be accomplished by liquid injection molding or by cast or compression molding or other types of molding. These processes are well known in the art. Suitable vulcanization temperatures for such processes are between 20-200° C. In an even more preferred embodiment, a polymer of the invention is used for the preparation of flexible intra-ocular lenses with high refractive index, preferably by a method known as injection molding, as such a method is cheap and rapid and produces high quality lenses.

The following non-limiting examples illustrate several embodiments of the present invention.

EXAMPLE 1

Monomer Route; Addition to the Monomer

Tetravinyl tetramethyl cyclo tetrasiloxane and triphenylsilane were mixed in a molar ratio of 1 to 4. An amount of 11 ppm of platinum divinyl tetramethyl disiloxane was added as a 2.5 wt. % solution in xylene. Air was excluded by replacing it with an argon atmosphere and the mixture was heated to 90° C. The mixture was stirred at the reaction temperature for 96 hours. After 96 hours, a small amount of vinyldiethylmethylsilane or another vinylcontaining silane was added and the mixture was stirred at 90° C. under argon atmosphere for 24 hours.

Monomer Route; Purification of the Modified Monomer (Optional)

After the addition reaction, the mixture was cooled to RT and 2 volume parts of methanol were added. After stirring for 4 hours in boiling methanol, stirring was stopped and the product was allowed to precipitate for 2 hours. Boiling methanol was decanted, 2 volumes of fresh methanol were added and the product was stirred in boiling methanol overnight. Again stirring was stopped, the product allowed to precipitate and boiling methanol was decanted. The material was dried in a vacuum oven at 70° C. to remove the methanol and cooled to RT thereafter.

A transparent glassy solid having a refractive index of 1.6-1.66 was obtained as determined by refractometry. NMR analysis showed that unreacted triphenylsilane was removed and that vinyl groups had almost completely disappeared (>92%). Instead, protons from bridging alkyl groups, resulting from the addition reaction, as well as protons from phenyl groups were present.

Monomer Route; Polymerization

The preparation of a (co)polymer from the triphenylsilane-modified tetravinyl tetramethyl cyclo tetrasiloxane monomer, can be performed by one of several ways:
  the resulting tetratriphenyl silylethane tetramethyl cyclo tetrasiloxane monomer (conversion vinyl groups >92%) may be allowed to react with other cyclic monomers such as e.g. octamethyl cyclo tetrasiloxane and tetravinyl tetramethyl cyclo tetrasiloxane (or equivalent cyclo siloxanes), or
  the resulting tetratriphenyl silylethane tetramethyl cyclo tetrasiloxane monomer conversion vinyl groups >92%) may be co-polymerised with (co)polymers such as poly-dimethylsiloxane or polydimethyl vinylmethylsiloxane or a combination of e.g. polydimethylsiloxane and tetravinyl tetramethyl cyclo tetrasiloxane monomers.

The following experiment serves as an illustration:

An amount of 1.2 g of the modified monomer (conversion vinyl groups >92%) was mixed with 1.0 g of octamethyl cyclo tetrasiloxane. In parallel experiments, a small amount of T or Q resin was added to improve the properties of the polymer. In other parallel experiments, small amounts of other monomers containing functional groups, for instance hydride or vinyl groups, were added. To these mixtures a small amount of potassium trimethyl silanolate was added as a catalyst. The mixture was stirred at 100° C. for 24 hours and at 150 to 200° C. for 120 hours under nitrogen atmosphere. A transparent polymer was obtained. After cooling to 100° C., 0.059 mg of tetravinyl tetramethyl cyclo tetrasiloxane was added and reaction allowed to proceed for 4 hours still under nitrogen atmosphere. After cooling to 50° C., dichloro dimethylsilane was added as a chain extender or chloro dimethyl vinylsilane was added as an endcapper. Alternatively, in methods such as described herein, e.g. trichlorosilanes or dichlorodiphenylsilanes may also be used as chain extenders.

The polymer was dried and heated and stirred in air at 90° C. for 2 hours or heated and stirred under argon atmosphere for 2 hours in the presence of divinyl tetramethyl disiloxane or, in parallel experiments in the presence of other vinyl-containing compounds such as 1,4-divinyl tetramethyl disilylethane and butadiene.

EXAMPLE 2

Polymer Route: Preparation of the (Pre)Polymer

An amount of 0.025 g potassium silanolate, 6.7 g tetravinyl tetramethyl cyclo tetrasiloxane, 13.3 g octamethyl cyclo tetrasiloxane and an amount of 40 µl divinyl tetramethyl disiloxane were mixed and reacted under argon atmosphere at 100° C. for 96 hours. After cooling to 50° C., 0.025 g of dimethyl vinylchlorosilane was added to the resulting copolymer and reacted under argon and stirring for 24 hours.

Polymer Route: Addition to the (Co)Copolymer

To the copolymer an amount of 10 ppm of platinum catalyst and an amount of triphenylsilane (sufficient as to provide 1 mole per mole of vinyl groups in the copolymer) were added. The mixture was stirred under argon atmosphere at 50° C. until 1-5 mole % of vinyl groups were left in the copolymer (determined with NMR analysis).

Polymer Route: Purification

After the addition reaction the mixture was cooled to RT and 2 volume parts of methanol were added. After stirring for 4 hours in boiling methanol, stirring was stopped and the product was allowed to precipitate for 2 hours. Boiling methanol was decanted, 2 volumes of fresh methanol were added and the product was stirred in boiling methanol overnight. Again stirring was stopped, the product was allowed to precipitate and boiling methanol was decanted. The material was dried overnight in a vacuum oven at 70° C. and then cooled.

The polymer was dried and heated and stirred in air at 90° C. for 2 hours or heated and stirred under argon atmosphere for 2 hours in the presence of divinyl tetramethyl disiloxane or, in parallel experiments in the presence of other vinyl-containing compounds such as 1,4-divinyl tetramethyl disilylethane and butadiene.

EXAMPLE 3

Manufacturing of an Intra-Ocular Lens (IOL):

The (co)polymer of example 1 was divided into two aliquots. To one part, hydride functional cross-linker (tetrakis-dimethylsiloxysilane) was added in a ratio of 1:1 hydride groups to vinyl groups in the material after mixing of the two parts. To the other part 10 ppm of platinum divinyl tetramethyl disiloxane was added. An amount of 0.1 wt. % of 1,2,3,4-tetramethyl-1,2,3,4-tetravinylcyclotetrasiloxane inhibitor, based on the weight of the polymer, was added to the part with the hydride cross-linker, and a benzophenone UV-blocker capable to react with the (co)polymer during the hydrosilylation curing (0.1 wt. %, based on the weight of the polymer) was added to both parts.

The two parts were mixed in an extruder and formation of IOL bodies was accomplished by liquid injection molding into a mold at a vulcanization temperature of 110° C. Post-curing was performed in an oven at a temperature of 120° C. for a periods of 2 hours. Highly transparent, foldable silicone IOL bodies of high refractive index of 1.50 were obtained.

We claim:

1. Monomeric cyclosiloxane comprising a clustered configuration of refractive index modifying groups chemically bonded to a cyclic siloxane backbone via an alkanediyl-bridge such that one alkanediyl-bridge binds at least two refractive index modifying groups to said backbone, wherein the refractive index modifying groups are independently selected from the group consisting of aromatic groups, aryl groups, arylalkyl groups, cycloalkyl groups and branched alkyl groups.

2. Monomeric cyclosiloxane according to claim 1, obtained by chemically modifying a cyclic siloxane by performing an addition reaction in the presence of an addition reaction catalyst which reaction links a clustered configuration of refractive index modifying groups to the siloxane backbone of said cyclic siloxane via an alkanediyl-bridge such that at least two of said refractive index modifying groups are bound to said backbone of said cyclic siloxane via a single alkanediyl-bridge.

3. Monomeric cyclosiloxane according to claim 2, wherein said cyclic siloxane is a chemically modified cyclic tetrasiloxane.

4. Monomeric cyclosiloxane according to claim 3, obtained by reacting cyclic tetrasiloxane with a triphenylsilane or triphenyl vinylsilane.

5. Monomeric cyclosiloxane according to claim 1, wherein the refractive index modifying groups are phenyl groups.

6. Monomeric cyclosiloxane obtained by reacting a cyclic siloxane of Formula II

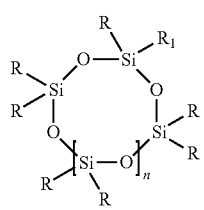

Formula II wherein

R is independently alkyl, vinyl or hydride;

$R_1$ is vinyl;

and n=0, 1, 2 or 3;

with triphenylsilane, diphenylsilane, triphenyl dimethyl disiloxane, phenyl dialkylsilane or diphenylalkyl dimethyl disiloxane in the presence of an addition reaction catalyst.

7. Monomeric cyclosiloxane obtained by reacting a cyclic siloxane of Formula II

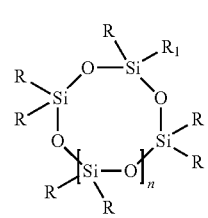

Formula II wherein

R is independently alkyl, vinyl or hydride;

$R_1$ is hydride;

and n=0, 1, 2 or 3;

with triphenyl, vinylsilane, diphenylalkyl, vinylsilane, phenyl dialkyl vinylsilane, triphenyl dimethyl vinyldisiloxane, diphenylethene, 3,3,3-triphenyl-1-propene, 3,3-diphenyl-1-propene or any other hydride reactive polyphenyl, in the presence of an addition reaction catalyst.

8. Method for preparing a monomeric cyclosiloxane comprising a clustered configuration of refractive index modifying groups comprising:

chemically modifying a cyclic siloxane by performing an addition reaction in the presence of an addition reaction catalyst which reaction links a clustered configuration of refractive index modifying groups to the siloxane backbone of said cyclic siloxane via an alkanediyl-bridge such that at least two of said refractive index modifying groups are bound to said backbone of said cyclic siloxane via a single alkanediyl-bridge, wherein the refractive index modifying groups are independently selected from the group consisting of aromatic groups, aryl groups, arylalkyl groups, cycloalkyl groups and branched alkyl groups.

9. Method for preparing a monomeric cyclosiloxane comprising a clustered configuration of refractive index modifying groups, comprising reacting a cyclic siloxane of Formula II

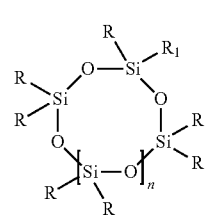

Formula II wherein

R is independently alkyl, vinyl or hydride;

$R_1$ is vinyl;

and n=0, 1, 2 or 3;

with triphenylsilane, diphenylsilane, triphenyl dimethyl disiloxane, phenyl dialkyl silane or diphenylalkyl dimethyl disiloxane in the presence of an addition reaction catalyst.

10. The method according to claim 9, wherein the cyclic siloxane of Formula II is reacted with triphenylsilane.

11. Method for preparing a monomeric cyclosiloxane comprising a clustered configuration of refractive index modifying groups, comprising reacting a cyclic siloxane of Formula II

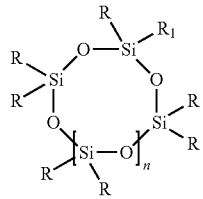

Formula II wherein
R is independently alkyl, vinyl or hydride;
$R_1$ is hydride;
and n=0, 1, 2 or 3;
with triphenyl vinylsilane, diphenylalkyl vinylsilane, phenyl dialkyl vinylsilane, triphenyl dimethyl vinyldisiloxane, diphenylethene, 3,3,3-triphenyl-1-propene, 3,3-diphenyl-1-propene or any other hydride reactive polyphenyl, in the presence of an addition reaction catalyst.

12. The method according to claim 11, wherein the cyclic siloxane of Formula II is reacted with triphenyl vinylsilane.

* * * * *